United States Patent
Zhang

(10) Patent No.: US 12,343,010 B2
(45) Date of Patent: Jul. 1, 2025

(54) STAPLING DEVICE WITH CURVED END EFFECTOR

(71) Applicant: Covidien LP, Mansfield, MA (US)

(72) Inventor: Jiangfeng Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/267,166

(22) PCT Filed: Dec. 17, 2020

(86) PCT No.: PCT/CN2020/137139
§ 371 (c)(1),
(2) Date: Jun. 14, 2023

(87) PCT Pub. No.: WO2022/126471
PCT Pub. Date: Jun. 23, 2022

(65) Prior Publication Data
US 2024/0090897 A1 Mar. 21, 2024

(51) Int. Cl.
*A61B 17/072* (2006.01)

(52) U.S. Cl.
CPC .. *A61B 17/072* (2013.01); *A61B 2017/07221* (2013.01); *A61B 2017/07257* (2013.01);
(Continued)

(58) Field of Classification Search
CPC . A61B 17/072; A61B 17/115; A61B 17/1155; A61B 17/1114; A61B 17/285; A61B 17/295; A61B 2017/07221; A61B 2017/07257; A61B 2017/07271; A61B 2017/07285; A61B 2017/320097; A61B 17/32053; A61B 17/3205; A61B 17/32;
(Continued)

(56) References Cited

U.S. PATENT DOCUMENTS

| | | |
|---|---|---|
| 1,158,111 A | 10/1915 | Ahlheim |
| 2,891,250 A | 6/1959 | Hirata |

(Continued)

FOREIGN PATENT DOCUMENTS

| | | |
|---|---|---|
| CN | 201189041 Y | 2/2009 |
| CN | 205285929 U | 6/2016 |

(Continued)

OTHER PUBLICATIONS

International Search Report for Application No. PCT/CN2020/137139 dated Sep. 15, 2021.
(Continued)

*Primary Examiner* — Stephen F. Gerrity
*Assistant Examiner* — Linda J Hodge

(57) ABSTRACT

An end effector for a transverse type surgical stapling device includes an anvil assembly and a cartridge assembly. The cartridge assembly includes a knife assembly having a knife blade and a guide pin. The guide pin is movable between retracted and advanced positions to confine tissue between the anvil assembly and the cartridge assembly. The end effector includes a body that supports a guide member that is spaced from the guide pin. The guide member and the guide pin are positioned and configured to engage the knife blade when the stapling device is fired to more effectively cut tissue clamped between the anvil and cartridge assemblies.

19 Claims, 9 Drawing Sheets

(52) U.S. Cl.
CPC .............. *A61B 2017/07271* (2013.01); *A61B 2017/07285* (2013.01)

(58) Field of Classification Search
CPC .... A61B 17/3201; A61B 10/0266; B26B 9/02
USPC ............................................ 433/144; 30/456
See application file for complete search history.

(56) References Cited

U.S. PATENT DOCUMENTS

| | | | |
|---|---|---|---|
| 3,080,564 A | 3/1963 | Strekopitov et al. | |
| 3,252,643 A | 5/1966 | Strekopov et al. | |
| 3,269,630 A | 8/1966 | Fleischer | |
| 3,275,211 A | 9/1966 | Hirsch et al. | |
| 3,315,863 A | 4/1967 | O'Dea | |
| 3,494,533 A | 2/1970 | Green et al. | |
| 3,589,589 A | 6/1971 | Akopov | |
| 3,692,224 A | 9/1972 | Astafiev et al. | |
| 3,795,034 A | 3/1974 | Strekopytov et al. | |
| 3,822,818 A | 7/1974 | Strekopytov et al. | |
| 3,935,981 A | 2/1976 | Akopov et al. | |
| 3,949,923 A | 4/1976 | Akopov et al. | |
| 4,047,654 A | 9/1977 | Alvarado | |
| 4,216,891 A | 8/1980 | Behlke | |
| 4,244,372 A | 1/1981 | Kapitanov et al. | |
| 4,296,881 A | 10/1981 | Lee | |
| 4,305,539 A | 12/1981 | Korolkov et al. | |
| 4,354,628 A | 10/1982 | Green | |
| 4,378,901 A | 4/1983 | Akopov et al. | |
| 4,383,634 A | 5/1983 | Green | |
| 4,402,444 A | 9/1983 | Green | |
| 4,415,112 A | 11/1983 | Green | |
| D273,513 S | 4/1984 | Spreckelmeier | |
| 4,442,964 A | 4/1984 | Becht | |
| 4,470,533 A | 9/1984 | Schuler | |
| 4,475,679 A | 10/1984 | Fleury, Jr. | |
| 4,485,811 A | 12/1984 | Chernousov et al. | |
| 4,506,670 A | 3/1985 | Crossley | |
| 4,506,671 A | 3/1985 | Green | |
| 4,508,253 A | 4/1985 | Green | |
| 4,522,327 A | 6/1985 | Korthoff et al. | |
| 4,527,724 A | 7/1985 | Chow et al. | |
| 4,530,453 A | 7/1985 | Green | |
| 4,550,870 A | 11/1985 | Krumme et al. | |
| 4,566,620 A | 1/1986 | Green et al. | |
| 4,568,009 A | 2/1986 | Green | |
| 4,573,622 A | 3/1986 | Green et al. | |
| 4,580,712 A | 4/1986 | Green | |
| 4,585,153 A | 4/1986 | Failla et al. | |
| 4,589,582 A | 5/1986 | Bilotti | |
| 4,602,634 A | 7/1986 | Barkley | |
| 4,605,001 A | 8/1986 | Rothfuss et al. | |
| 4,605,004 A | 8/1986 | Di Giovanni et al. | |
| 4,606,344 A | 8/1986 | Di Giovanni | |
| 4,606,345 A | 8/1986 | Dorband et al. | |
| 4,607,636 A | 8/1986 | Kula et al. | |
| 4,612,933 A | 9/1986 | Brinkerhoff et al. | |
| 4,617,928 A | 10/1986 | Alfranca | |
| 4,632,290 A | 12/1986 | Green et al. | |
| 4,665,916 A | 5/1987 | Green | |
| 4,684,051 A | 8/1987 | Akopov et al. | |
| 4,714,187 A | 12/1987 | Green | |
| 4,715,520 A | 12/1987 | Roehr, Jr. et al. | |
| 4,728,020 A | 3/1988 | Green et al. | |
| 4,767,044 A | 8/1988 | Green | |
| 4,788,978 A | 12/1988 | Strekopytov et al. | |
| 4,802,614 A | 2/1989 | Green et al. | |
| 4,805,823 A | 2/1989 | Rothfuss | |
| 4,819,853 A | 4/1989 | Green | |
| 4,848,637 A | 7/1989 | Pruitt | |
| 4,869,414 A | 9/1989 | Green et al. | |
| 4,881,544 A | 11/1989 | Green et al. | |
| 4,881,545 A | 11/1989 | Isaacs et al. | |
| 4,915,100 A | 4/1990 | Green | |
| 4,930,503 A | 6/1990 | Pruitt | |
| 1,941,623 A | 7/1990 | Pruitt | |
| 4,938,408 A | 7/1990 | Bedi et al. | |
| 4,951,861 A | 8/1990 | Schulze et al. | |
| 4,964,559 A | 10/1990 | Deniega et al. | |
| 4,967,477 A * | 11/1990 | Sanford | B26B 27/00 30/314 |
| 5,005,754 A | 4/1991 | Van Overloop | |
| 5,018,657 A | 5/1991 | Pedlick et al. | |
| 5,071,052 A | 12/1991 | Rodak et al. | |
| 5,100,042 A | 3/1992 | Gravener et al. | |
| 5,116,349 A | 5/1992 | Aranyi | |
| 5,137,198 A | 8/1992 | Nobis et al. | |
| 5,172,845 A | 12/1992 | Tejeiro | |
| 5,190,203 A | 3/1993 | Rodak | |
| 5,219,111 A | 6/1993 | Bilotti et al. | |
| 5,240,163 A | 8/1993 | Stein et al. | |
| 5,344,060 A | 9/1994 | Gravener et al. | |
| 5,368,599 A | 11/1994 | Hirsch et al. | |
| 5,405,073 A | 4/1995 | Porter | |
| 5,413,267 A | 5/1995 | Solyntjes et al. | |
| 5,439,155 A | 8/1995 | Viola | |
| 5,452,836 A | 9/1995 | Huitema et al. | |
| 5,458,279 A | 10/1995 | Plyley | |
| 5,462,215 A | 10/1995 | Viola et al. | |
| 5,464,144 A | 11/1995 | Guy et al. | |
| 5,465,894 A | 11/1995 | Clark et al. | |
| 5,470,006 A | 11/1995 | Rodak | |
| 5,470,008 A | 11/1995 | Rodak | |
| 5,470,009 A | 11/1995 | Rodak | |
| 5,497,934 A | 3/1996 | Brady et al. | |
| 5,503,320 A | 4/1996 | Webster et al. | |
| 5,509,596 A | 4/1996 | Green et al. | |
| 5,542,594 A | 8/1996 | McKean et al. | |
| 5,547,117 A | 8/1996 | Hamblin et al. | |
| 5,558,266 A | 9/1996 | Green et al. | |
| 5,571,285 A | 11/1996 | Chow et al. | |
| 5,579,978 A | 12/1996 | Green et al. | |
| 5,580,067 A | 12/1996 | Hamblin et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,615,820 A | 4/1997 | Viola | |
| 5,641,111 A | 6/1997 | Ahrens et al. | |
| 5,678,748 A | 10/1997 | Plyley et al. | |
| 5,697,543 A | 12/1997 | Burdorf | |
| 5,706,997 A | 1/1998 | Green et al. | |
| 5,706,998 A | 1/1998 | Plyley et al. | |
| 5,709,697 A * | 1/1998 | Ratcliff | A61B 17/320016 606/167 |
| 5,732,871 A | 3/1998 | Clark et al. | |
| 5,735,445 A | 4/1998 | Vidal et al. | |
| 5,794,834 A | 8/1998 | Hamblin et al. | |
| 5,810,240 A | 9/1998 | Robertson | |
| 5,855,311 A | 1/1999 | Hamblin et al. | |
| 5,878,937 A | 3/1999 | Green et al. | |
| 5,893,506 A | 4/1999 | Powell | |
| 5,894,979 A | 4/1999 | Powell | |
| 5,964,394 A | 10/1999 | Robertson | |
| 6,045,560 A | 4/2000 | McKean et al. | |
| 6,638,285 B2 | 10/2003 | Gabbay | |
| 6,805,273 B2 | 10/2004 | Bilotti et al. | |
| 6,817,508 B1 | 11/2004 | Racenet et al. | |
| 6,988,650 B2 | 1/2006 | Schwemberger et al. | |
| 7,070,083 B2 | 7/2006 | Jankowski | |
| 7,134,587 B2 | 11/2006 | Schwemberger et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,210,609 B2 | 5/2007 | Leiboff et al. | |
| 7,237,708 B1 | 7/2007 | Guy et al. | |
| 7,275,674 B2 | 10/2007 | Racenet et al. | |
| RE40,237 E | 4/2008 | Bilotti et al. | |
| 7,407,076 B2 | 8/2008 | Racenet et al. | |
| 7,431,190 B2 | 10/2008 | Hoffman | |
| 7,522,854 B2 | 4/2009 | Kinouchi et al. | |
| 7,549,563 B2 | 6/2009 | Mather et al. | |
| 7,568,605 B2 | 8/2009 | Kruszynski | |
| 7,641,092 B2 | 1/2010 | Kruszynski et al. | |

(56) References Cited

U.S. PATENT DOCUMENTS

| | | |
|---|---|---|
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,328,064 B2* | 12/2012 | Racenet ............... A61B 17/115 227/176.1 |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 9,192,387 B1 | 11/2015 | Holsten et al. |
| 9,480,474 B2 | 11/2016 | Ji et al. |
| 9,566,066 B2 | 2/2017 | Kasvikis |
| 9,579,102 B2 | 2/2017 | Holsten et al. |
| 9,655,619 B2 | 5/2017 | Zhang et al. |
| 9,662,111 B2 | 5/2017 | Holsten et al. |
| 9,668,736 B2 | 6/2017 | Holsten et al. |
| 9,675,349 B2 | 6/2017 | Holsten et al. |
| 9,675,350 B2 | 6/2017 | Holsten et al. |
| 9,675,356 B2 | 6/2017 | Racenet et al. |
| 9,814,460 B2 | 11/2017 | Kimsey et al. |
| 9,888,923 B2 | 2/2018 | Chen et al. |
| 9,962,159 B2 | 5/2018 | Heinrich et al. |
| 10,004,504 B2 | 6/2018 | Bryant |
| 10,045,780 B2* | 8/2018 | Adams ............. A61B 17/00234 |
| 10,085,754 B2 | 10/2018 | Sniffin et al. |
| 10,194,913 B2 | 2/2019 | Nalagatla et al. |
| 10,485,542 B2* | 11/2019 | Shelton, IV ..... A61B 17/07207 |
| 11,944,310 B2* | 4/2024 | Shelton, IV ....... A61B 17/1155 |
| 2004/0164123 A1 | 8/2004 | Racenet et al. |
| 2005/0065542 A1* | 3/2005 | Mansfield .......... A61B 17/3213 606/167 |
| 2005/0139629 A1* | 6/2005 | Schwemberger .... A61B 17/072 227/19 |
| 2005/0145673 A1 | 7/2005 | Nguyen et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0187456 A1 | 8/2007 | Viola et al. |
| 2010/0048988 A1 | 2/2010 | Pastorelli et al. |
| 2010/0180452 A1* | 7/2010 | Mucci ...................... B26B 9/02 30/356 |
| 2010/0263212 A1* | 10/2010 | Settele .................... A47J 25/00 30/113.1 |
| 2011/0136075 A1* | 6/2011 | Park ........................ A61C 3/02 433/144 |
| 2013/0206813 A1 | 8/2013 | Nalagatla |
| 2014/0309666 A1* | 10/2014 | Shelton, IV ..... A61B 17/07207 606/139 |
| 2016/0249914 A1 | 9/2016 | Zhang et al. |
| 2016/0249923 A1 | 9/2016 | Hodgkinson et al. |
| 2016/0270784 A1 | 9/2016 | Wheeler et al. |
| 2016/0270790 A1 | 9/2016 | Jankowski |
| 2016/0270793 A1 | 9/2016 | Carter et al. |
| 2016/0278779 A1 | 9/2016 | Jankowski |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055960 A1* | 3/2017 | Kattine ............. A61B 10/0266 |
| 2017/0128149 A1 | 5/2017 | Heinrich et al. |
| 2017/0238923 A1 | 8/2017 | Holsten et al. |
| 2017/0238924 A1 | 8/2017 | Holsten et al. |
| 2017/0265861 A1 | 9/2017 | Holsten et al. |
| 2018/0008261 A1 | 1/2018 | Racenet et al. |
| 2018/0049739 A1 | 2/2018 | Kasvikis |
| 2018/0153544 A1* | 6/2018 | Maddur Shankarsetty ................. A61B 90/90 |
| 2018/0221024 A1 | 8/2018 | Heinrich et al. |
| 2018/0264661 A1* | 9/2018 | Hauser .................... A47J 17/02 |
| 2019/0159775 A1 | 5/2019 | Maddur et al. |

FOREIGN PATENT DOCUMENTS

| | | | | |
|---|---|---|---|---|
| CN | 106923874 | * | 7/2017 | ........... A61B 17/072 |
| EP | 3730068 A1 | * | 10/2020 | ........... A61B 17/072 |
| WO | WO-2014043971 A1 | * | 3/2014 | ........... A61B 17/072 |

OTHER PUBLICATIONS

Written Opinion for Application No. PCT/CN2020/137139 dated Sep. 15, 2021.

* cited by examiner

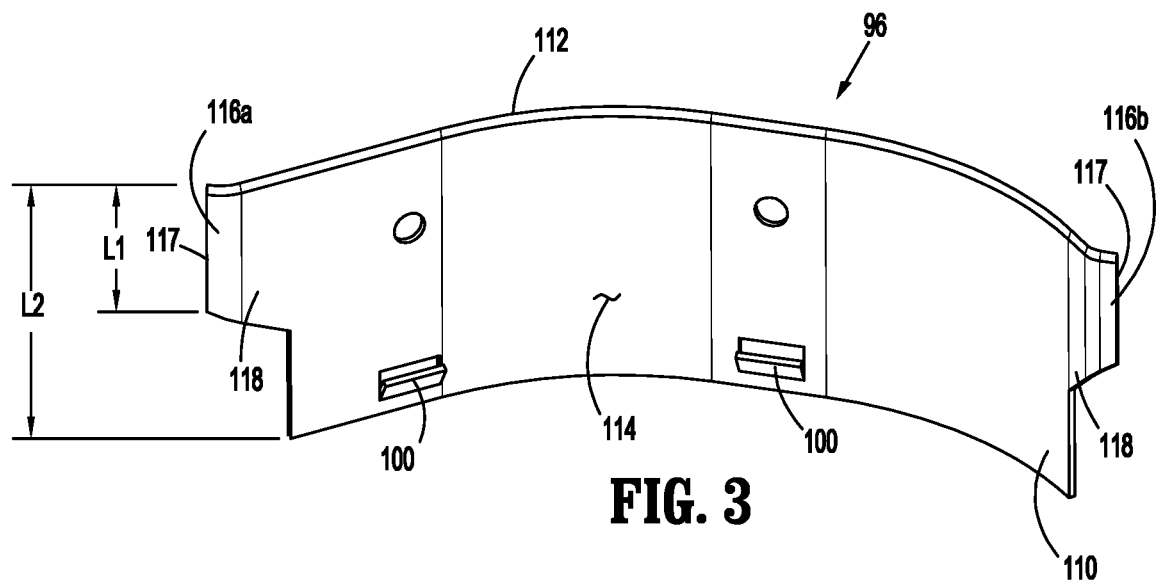
FIG. 3
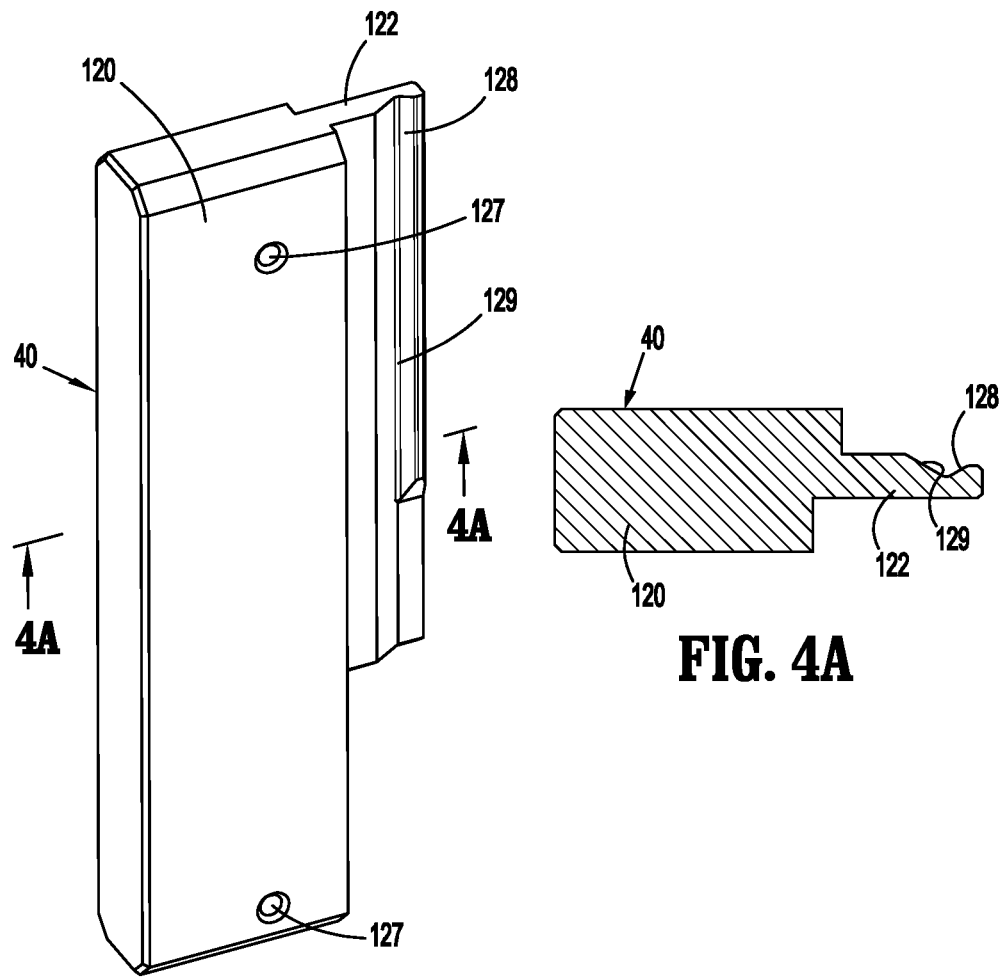
FIG. 4
FIG. 4A

STAPLING DEVICE WITH CURVED END EFFECTOR

FIELD

The present technology is generally related to surgical stapling devices and, more particularly, to surgical stapling devices that have a curved end effector including a knife blade.

BACKGROUND

Surgical stapling devices are commonly used during a variety of surgical procedures to expedite dissection and suturing of tissue and minimize trauma to a patient. Typically, the stapling devices include an end effector that includes a cartridge assembly and an anvil assembly. The cartridge assembly includes a knife assembly with a knife blade that has a sharpened cutting edge which is driven through tissue to transect or resect the tissue.

Surgical stapling devices are available in a variety of types for performing a variety of different surgical procedures. One type of stapling device includes a U-shaped end effector that has a first transverse portion, a second transverse portion, and a longitudinal portion that interconnects the first transverse portion with the second transverse portion. Each of the first and second transverse portions has a first end coupled to the longitudinal portion and a second end. The seconds ends of the first and second transverse portions are spaced from each other to define an opening for receiving tissue. The anvil assembly is supported on the first transverse portion and the cartridge assembly is supported adjacent the second transverse portion. Typically, the cartridge assembly includes a cartridge body, a guide pin, and a knife assembly. The guide pin is movable from a retracted position in which the pin is positioned within the cartridge body to an advanced position in which the guide pin extends from the cartridge body and engages the anvil assembly to close the opening defined between the second ends of the first and second transverse portions and capture tissue within the end effector between the anvil and cartridge assemblies.

During a surgical procedure, the cartridge assembly is moved towards the first transverse portion to move the stapling device from an open position to a clamped position and clamp tissue, e.g., the colon, between the anvil and cartridge assemblies. The guide pin is also moved to its advanced position to confine the tissue between the anvil and cartridge assemblies as the tissue is being clamped. When the stapling device is fired, the knife assembly moves from its retracted position to its advanced position to cut tissue clamped between the anvil and cartridge assemblies. In some instances, the tissue clamped between the anvil and cartridge assemblies is compressed outwardly of the knife assembly is not cleanly cut.

A continuing need exists in the art for an end effector that can more effectively cut tissue clamped between the anvil and cartridge assemblies when the stapling device is fired.

SUMMARY

Aspects of this disclosure are directed to an end effector for a transverse type surgical stapling device that includes an anvil assembly and a cartridge assembly. The cartridge assembly includes a knife assembly having a knife blade and a guide pin. The guide pin is movable between retracted and advanced positions to confine tissue between the anvil assembly and the cartridge assembly. The end effector includes a body that supports a guide member that is spaced from the guide pin. The guide member and the guide pin are positioned and configured to engage the knife blade when the stapling device is fired to more effectively cut tissue clamped between the anvil and cartridge assemblies.

Aspects of this disclosure are directed to a stapling device including a handle portion, an elongate body, and an end effector. The elongate body defines a longitudinal axis and extends distally from the handle portion. The end effector is supported on the elongate body and includes a body, a guide member, an anvil assembly, and a cartridge assembly. The body includes a first portion, a second portion, and a longitudinal portion that interconnects the first and second portions. The first and second portions extend in a direction transverse to the longitudinal axis and have corresponding curved configurations. The first and second portions have first and second ends. The first portion is spaced from the second portion to define a cavity therebetween that is closed at the first ends of the first and second portions by the longitudinal portion. The second ends of the first and second portions are spaced from each other to define an opening. The guide member is secured to the longitudinal portion of the body of the end effector and includes a guide portion that extends into the cavity and defines an angled guide surface. The anvil assembly is supported on the first portion of the body of the end effector. The cartridge assembly includes a cartridge body, a pusher, a knife assembly, and a guide pin. The cartridge body defines a body cavity, staple receiving slots, and a knife slot. The staple receiving slots are positioned on opposite sides of the knife slot and receive staples. The pusher is movable within the body cavity from a retracted position to an advanced position to eject the staples from the cartridge body. The knife assembly includes a curved knife blade that is movable from a retracted position recessed within the cartridge body to an advanced position extending through the knife slot of the cartridge body. The guide pin includes an angled guide surface and is movable from a retracted position located within the cartridge body to an advanced position extending from the cartridge body. The guide pin is engaged with the anvil assembly in its advanced position to close the opening defined by the body of the end effector. The knife blade has a curved configuration that corresponds to the curved configuration of the first and second portions of the body of the end effector and includes first and second bent end portions. The first bent end portion is engaged with the angled guide surface of the guide member and the second bent end portion is engaged with the angled guide surface of the guide pin.

Other aspects of this disclosure are directed to an end effector that includes a body, a guide member, an anvil assembly, and a cartridge assembly. The body includes a first portion, a second portion, and a longitudinal portion that interconnects the first and second portions. The first and second portions extend in a direction transverse to the longitudinal portion and have corresponding curved configurations. The first and second portions have first and second ends. The first portion is spaced from the second portion to define a cavity therebetween that is closed at the first ends of the first and second portions by the longitudinal portion. The second ends of the first and second portions are spaced from each other to define an opening therebetween. The guide member is secured to the longitudinal portion of the body of the end effector and includes a guide portion that extends into the cavity and defines a first angled guide surface. The anvil assembly is supported on the first portion of the body of the end effector. The cartridge assembly includes a cartridge body, a pusher, a knife assembly, and a guide pin. The cartridge body defines a cavity, staple receiving slots, and a knife slot. The staple receiving slots are positioned on opposite sides of the knife slot and includes staples. The pusher is movable within the body cavity from a retracted position to an advanced position to eject the staples from the cartridge body. The knife assembly includes a curved knife blade that is movable from a retracted position recessed within the cartridge body to an advanced position extending through the knife slot of the cartridge body. The guide pin includes a second angled guide surface and is movable from a retracted position located within the cartridge body to an advanced position extending from the cartridge body. The guide pin is engaged with the anvil assembly in its advanced position to close the opening defined by the body of the end effector. The knife blade has a curved configuration that corresponds to the curved configuration of the first and second portions of the body of the end effector and includes first and second bent end portions. The first bent end portion is engaged with the first angled guide surface of the guide member and the second bent end portion is engaged with the second angled guide surface of the guide pin.

In aspects of the disclosure, the knife blade has a concave side and a convex side and the first and second bent end portions are angled in a direction of the convex side of the knife blade away from the concave side.

In some aspects of the disclosure, the knife blade includes a distal portion that defines a cutting edge.

In certain aspects of the disclosure, the cutting edge extends along the first and second bent end portions of the knife blade.

In aspects of the disclosure, the guide member includes a body portion that is secured to the longitudinal portion of the body of the end effector.

In some aspects of the disclosure, the guide portion extends from the body portion of the guide member into the cavity defined by the body of the end effector.

In certain aspects of the disclosure, the guide portion defines a longitudinally extending concavity that is defined in part by the angled guide surface of the guide portion.

In aspects of the disclosure, the knife assembly includes a knife holder, and the knife blade is secured to and extends distally from the knife holder.

In some aspects of the disclosure, the anvil assembly includes an anvil member and a cutting plate that is sandwiched between the first portion of the body of the end effector and the anvil member.

In certain aspects of the disclosure, the second portion of the body of the end effector defines a first channel, and the cartridge assembly is removably received within the first channel of the second portion of the body of the end effector.

In aspects of the disclosure, the knife blade includes a central body portion and wings that extend outwardly from the central body portion.

In some aspects of the disclosure, the first and second bent end portions of the knife blade extend outwardly from the wings.

In certain aspects of the disclosure, the guide pin defines a flat and the flat and the second angled guide surface of the guide pin define axes that intersect to define an acute angle.

In aspects of the disclosure, the guide pin has a proximal portion that is connected to a pin coupler.

Still other aspects of this disclosure are directed to a knife blade including a body having a curved configuration. The body includes a central portion and first and second bent end portions. The body has a concave side, a convex side, a distal portion, and a proximal portion. The first and second bent end portions are angled in a direction of the convex side of the knife blade away from the concave side. The distal portion of the body defines a cutting edge that extends along the first and second bent end portions.

Other features of the disclosure will be appreciated from the following description.

BRIEF DESCRIPTION OF THE DRAWINGS

Various aspects of the disclosure are described herein below with reference to the drawings, wherein:

FIG. 3 is a perspective view of a knife blade of a knife assembly of a cartridge assembly of the end effector shown in FIG. 2;

FIG. 4 is a side perspective view of a guide member of the end effector shown in FIG. 2;

FIG. 4A is a cross-sectional view taken along section line 4A-4A of FIG. 2;

DETAILED DESCRIPTION

Figure 1:
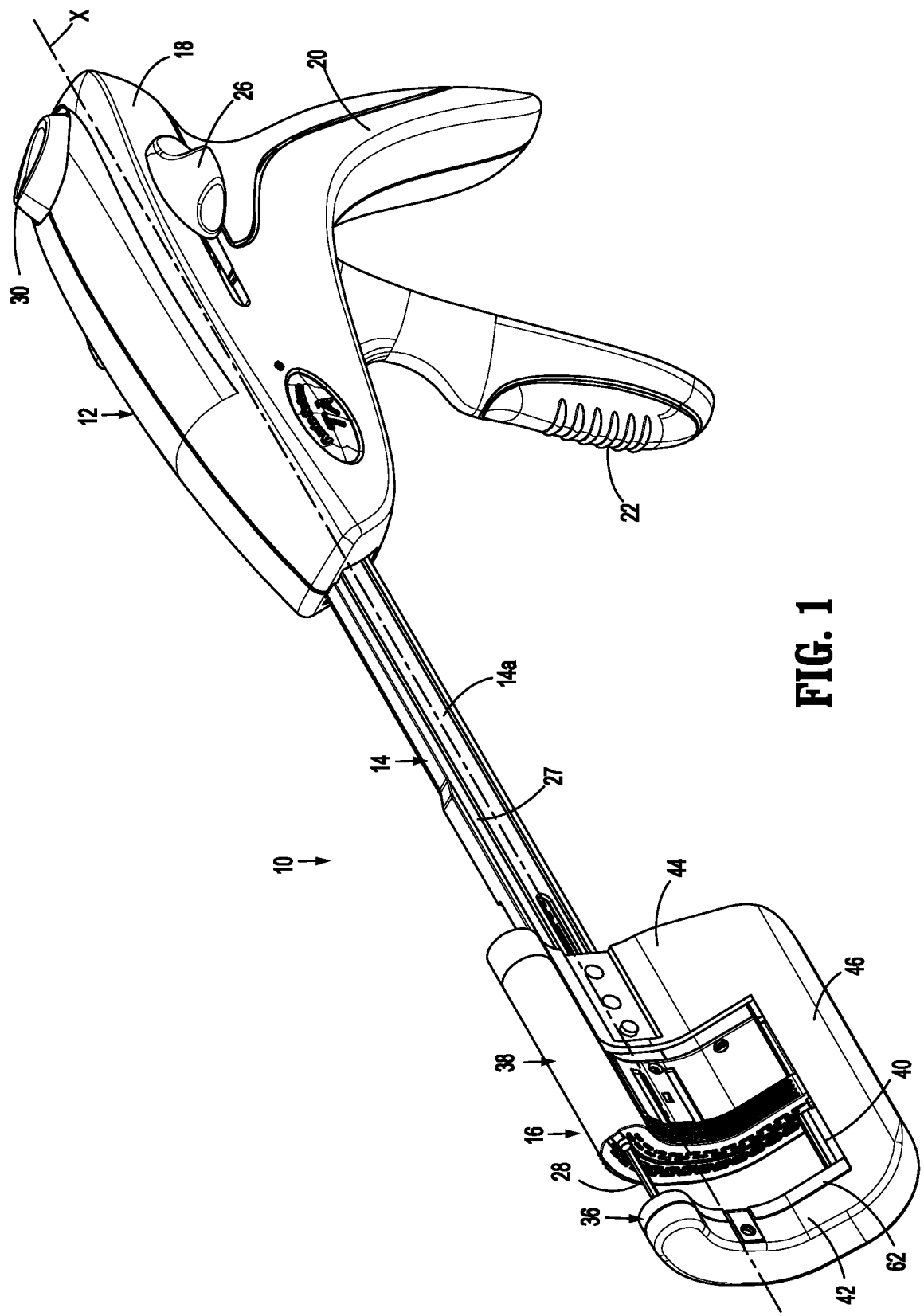
FIG. 1 is a side perspective view of a surgical stapling device including an end effector according to aspects of the disclosure with the end effector in an open position and an alignment pin of a cartridge assembly of the end effector in an advanced position.

The disclosed surgical stapling device will now be described in detail with reference to the drawings in which like reference numerals designate identical or corresponding elements in each of the several views. However, it is to be understood that the aspects of the disclosure are merely exemplary and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, and support personnel. "About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±10% of the stated value.

FIG. 1 illustrates the disclosed surgical stapling device shown generally as stapling device 10. The stapling device 10 includes a handle assembly 12, an elongate body 14 that extends distally from the handle assembly 12, and an end effector 16 that is supported on a distal portion of the elongate body 14. The elongate body 14 defines a longitudinal axis "X" and includes an elongate frame 14a that extends between the handle assembly 12 and the end effector 16. The handle assembly 12 includes a housing 18 that defines a stationary handle 20 and supports a movable trigger 22. In aspects of the disclosure, the movable trigger 22 is supported by the housing 18 to pivot towards the stationary handle 20 between non-actuated and actuated positions to operate the end effector 16. The handle assembly 12 also supports buttons 26 (only one is shown) that are positioned on opposite sides of the housing 18 and are movable along the housing 18 to advance and retract a guide pin pusher 27. The guide pin pusher 27 is positioned and configured to engage a guide pin 28 within the end effector 16 to move an alignment pin 28 between a retracted position and an advanced position (FIG. 1). The handle assembly 12 also includes a release button 30 that can be depressed to move the end effector 16 from a clamped or partially clamped position to an unclamped position. For a more detailed description of a handle assembly 12 and elongate body 14 of a similar stapling device, see, e.g., U.S. Pat. No. 6,817,508 ("the '508 patent").

Figure 2:
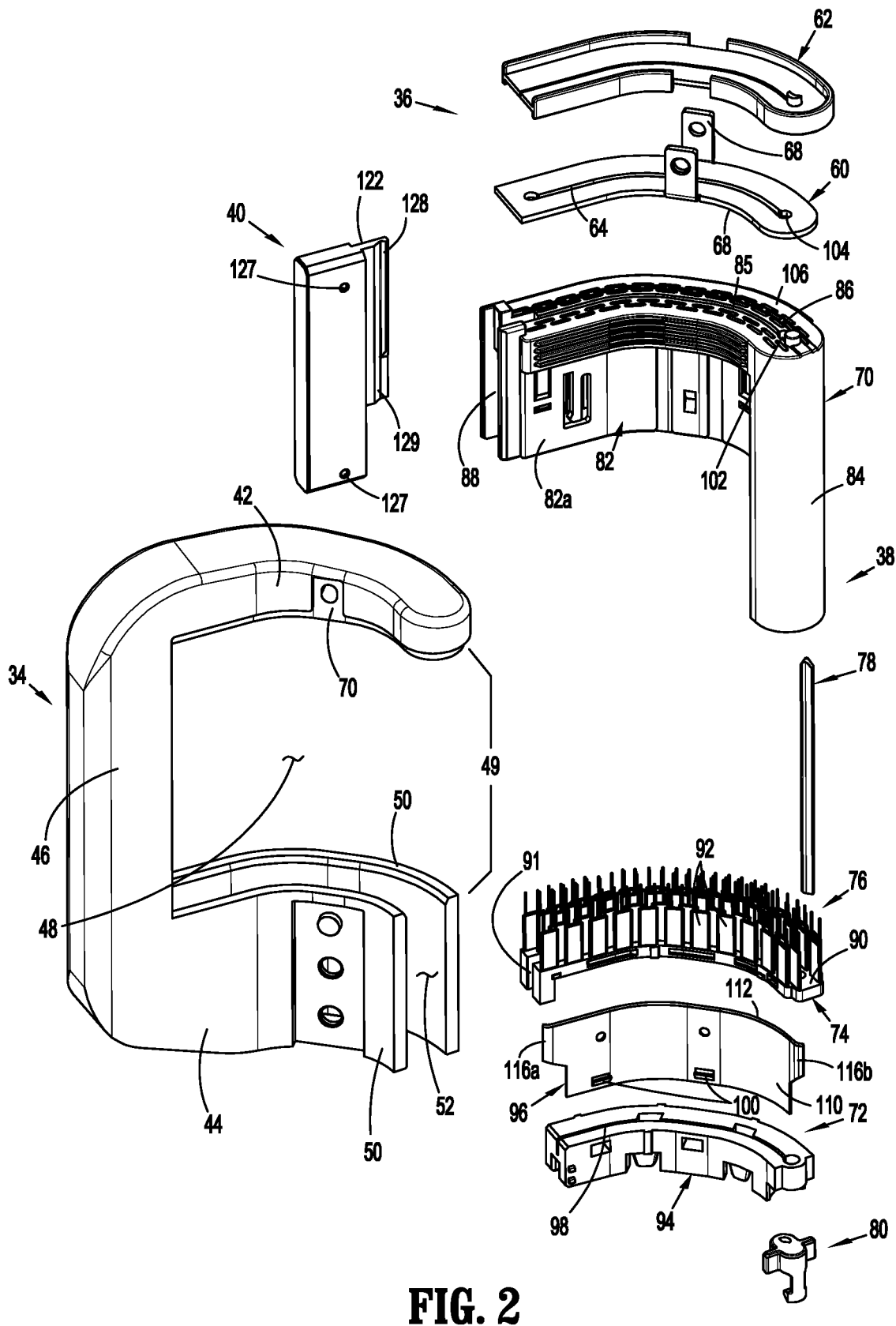
FIG. 2 is an exploded view of the end effector of the stapling device shown in FIG. 1.

FIGS. 1 and 2 illustrate the end effector 16 of the stapling device 10 which includes a body 34, and anvil assembly 36, a cartridge assembly 38, and a guide member 40. The body 34 has a U-shaped configuration and includes a first transverse portion 42, a second transverse portion 44, and a longitudinal portion 46 that couples the first transverse portion 42 to the second transverse portion 44. The first transverse portion 42 is positioned distally of the second transverse portion 44 to define a cavity 48 (FIG. 2) that is enclosed on a first side of the body 34 by the longitudinal portion 46 of the body 34. The ends of the first and second transverse portions 42 and 44 spaced from the longitudinal portion 46 define an opening 49 (FIG. 2) into the cavity 48. The second transverse portion 44 includes first and second spaced side walls 50 that define a channel 52 that is positioned proximally of the cavity 48. In aspects of the disclosure, the first and second transverse portions 42 and 44 extend in a direction transverse to the longitudinal axis "X" of the elongate body 14 and have corresponding curved configurations. Alternately, it is envisioned that the transverse portions of the body 34 of the end effector 16 may have other linear or curved configurations.

The anvil assembly 36 has a configuration that corresponds to the configuration of the first transverse portion 42 of the body 34 and includes an anvil member 60 and a cutting plate 62. In aspects of the disclosure, the anvil member 60 defines a curved knife slot 64 and has a proximally facing staple forming surface 66. In some aspects of the disclosure, the anvil member 60 includes proximally extending flanges 66 that are secured within recesses 70 formed in the first transverse portion 42 of the body 34 of the end effector 16 to secure the anvil member 60 to the first transverse portion 42 of the body 34. The cutting plate 62 is received on the first transverse portion 42 of the body 34 of the end effector 16 and is sandwiched between the anvil member 60 and the first transverse portion 42 of the body 34. In some aspects of the disclosure, the flanges 68 of the anvil member 60 are secured to the first transverse portion 42 of the body 34 using screws or rivets (not shown). Alternately, other fastening devices or techniques can be used to secure the anvil assembly 36 to the body 34 of the end effector 16 including welds, crimping, or the like.

The cartridge assembly 38 includes a cartridge body 70, a knife assembly 72, a pusher 74, staples 76, a guide pin 78, and a guide pin coupler 80. The cartridge body 70 has a distal portion 82 that has a curved configuration that corresponds to the configuration of the second transverse portion 44 of the body 34 of the end effector 34 and an elongate proximal portion 84 that extends proximally from the distal portion 82. The distal portion 82 of the cartridge body 70 defines a curved knife slot 85 and a plurality of staple receiving slots 86 that are positioned on opposite sides of the curved knife slot 85. In aspects of the disclosure, the staple receiving slots 86 are aligned in one or more rows (e.g., 2 or 3) on each side of the curved knife slot 85. Each of the staple receiving slots 86 receives one of the staples 76. In aspects of the disclosure, the curvature of the knife slot 85 corresponds to the curvature of the distal portion 82 of the cartridge body 70.

The cartridge body 70 defines a cavity 88 (FIG. 2) that receives the pusher 74 and the knife assembly 72. The pusher 74 has a curved configuration and is movable within the cavity 88 of the cartridge body 70 between retracted and advanced positions. The pusher 74 includes a base portion 90 and a plurality of fingers 92 that are received in the staple receiving slots 86 of the cartridge body 70. The base portion 90 defines a curved knife slot 91 and the fingers 92 are positioned on opposite sides of the knife slot 91. Each of the fingers 92 (FIG. 2) is received within a respective one of the staple receiving slots 86 and supports a staple 76 such that movement of the pusher 74 within the cavity 88 of the cartridge body 70 from its retracted position towards its advanced position forces the staples 76 from the cartridge body 70 towards the anvil assembly 36.

The knife assembly 72 is positioned within the cavity 88 of the cartridge body 70 proximally of the pusher 74 and includes a knife holder 94 and a knife blade 96. The knife blade 96 is secured to and extends distally from the knife holder 94 through the curved knife slot 91 in the pusher 74 and into the curved knife slot 85 in the cartridge body 74. In aspects of the disclosure, a proximal portion of the knife blade 96 is received within a slot 98 defined in the knife holder 94 to secure the knife blade 96 to the knife holder 94. In aspects of the disclosure, the proximal portion of the knife blade 96 includes barbs or tangs 100 that prevent removal of the knife blade 96 from the knife holder 94. Alternately, the knife blade 96 can be secured to the knife holder 94 using a variety of different securement devices or techniques. When the knife assembly 72 is moved from its retracted position to its advanced position, the knife assembly 72 moves in relation to the pusher 74 to advance the knife blade 96 through the curved knife slot 91 of the pusher 74 and through the curved knife slot 85 of the cartridge body 70 to a position in which the knife blade 96 projects distally from the cartridge body 70 into the anvil assembly 36.

A proximal portion of the guide pin 78 is coupled to the guide pin coupler 80. The guide pin 78 and the guide pin coupler 80 are supported within the proximal portion 84 of the cartridge body 70 and are movable between a retracted position and an advanced position. In the retracted position, the guide pin 78 is positioned entirely within the cartridge body 70. The cartridge body 70 defines a through bore 102 that extends through a distal face 106 of the cartridge body 70. The guide pin 78 is longitudinally aligned with the through bore 102. When the guide pin 78 is moved to the advanced position, the guide pin 78 moves through the through bore 102, across the opening 49 defined by the end effector body 34, and into a bore 104 defined in the anvil assembly 36 to close the opening 49.

The cartridge body 82 of the cartridge assembly 38 includes a proximal portion 82*a* that is received within the channel 52 defined by the second transverse portion 44 of the body 34 of the end effector 16. As the cartridge assembly 36 is received within the channel 52 of the end effector 16, the cartridge assembly 38 also engages a clamp slide assembly (not shown) of the stapling device 10 and the knife assembly 72 engages a thrust bar (not shown) of the stapling device 10. In addition, the guide pin coupler 80 engages a distal portion the guide pin pusher 27 (FIG. 1). With the cartridge assembly 38 supported within the clamp slide assembly (not shown), the cartridge assembly 38 can be moved with the clamp slide assembly within the cavity 48 (FIG. 2) of the body 34 of the end effector 16 between the open and clamped positions. The knife assembly 38 and the guide pin 78 can be moved between their advanced and retracted positions via actuation of the handle assembly 12. For a more detailed description of the guide pin pusher, clamp slide assembly, and the thrust bar, see, e.g., the '508 patent.

FIGS. 2 and 3 illustrate the knife blade 96 which includes a curved body 110 having a proximal portion and a distal portion. The curved body 110 has a configuration that corresponds to the curved configuration of the distal portion 82 (FIG. 2) of the cartridge body 70. The distal portion of the curved body 110 defines a cutting edge 112 and the proximal portion of the curved body 110 includes the barbs 100 which, as described above, facilitate attachment of the knife blade 96 to the knife holder 94. The curved body 110 has a concave side that defines a concavity 114 and a convex side. The curved body 110 includes first and second bent end portions 116*a* and 116*b*, respectively, that are positioned between distal and proximal ends of the knife blade 96 and bend towards the convex side of the knife blade 96. In aspects of the disclosure, the first and second bent end portions 116*a* and 116*b* are formed on wings 118 that extend outwardly from a central portion of the curved body 110 and have a length "L1" (FIG. 3) that is shorter than the length "L2" of the curved body 110 of the knife blade 96. In aspects of the disclosure, the first and second bent end portions 116*a* and 116*b* are angled in a direction away from the concavity 114 defined by the curved body 110 of the knife blade 96 such that outer edges 117 of the first and second bent end portions 116*a* and 116*b* are positioned on the convex side of the knife blade 96. In certain aspects of the disclosure, the first and second bent end portions 116*a* and 116*b* have a distal cutting edge that is contiguous with the cutting edge 112.

Figure 9:
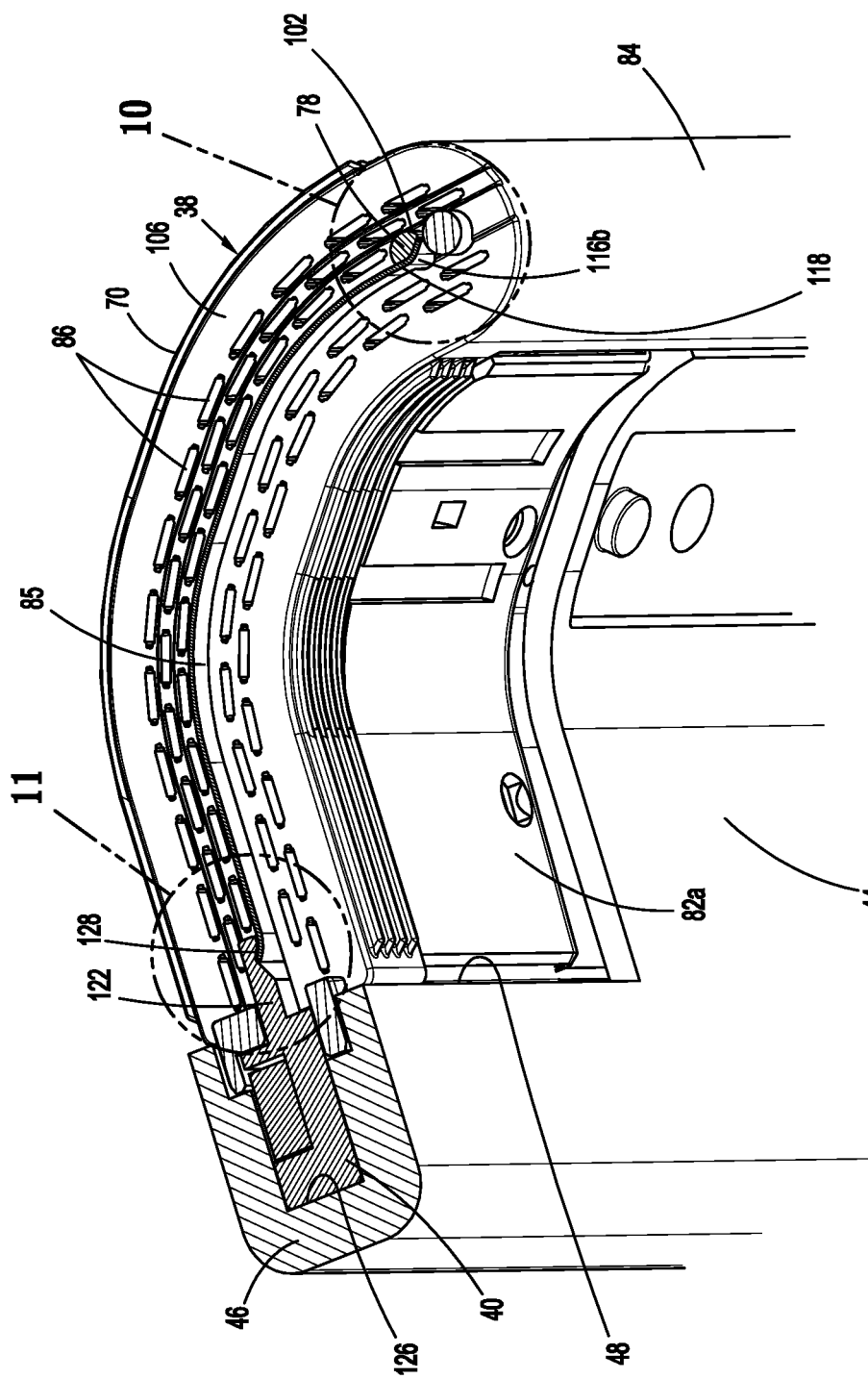
FIG. 9 is a cross-sectional view taken along section line 9-9 of FIG. 6.
Figure 10:
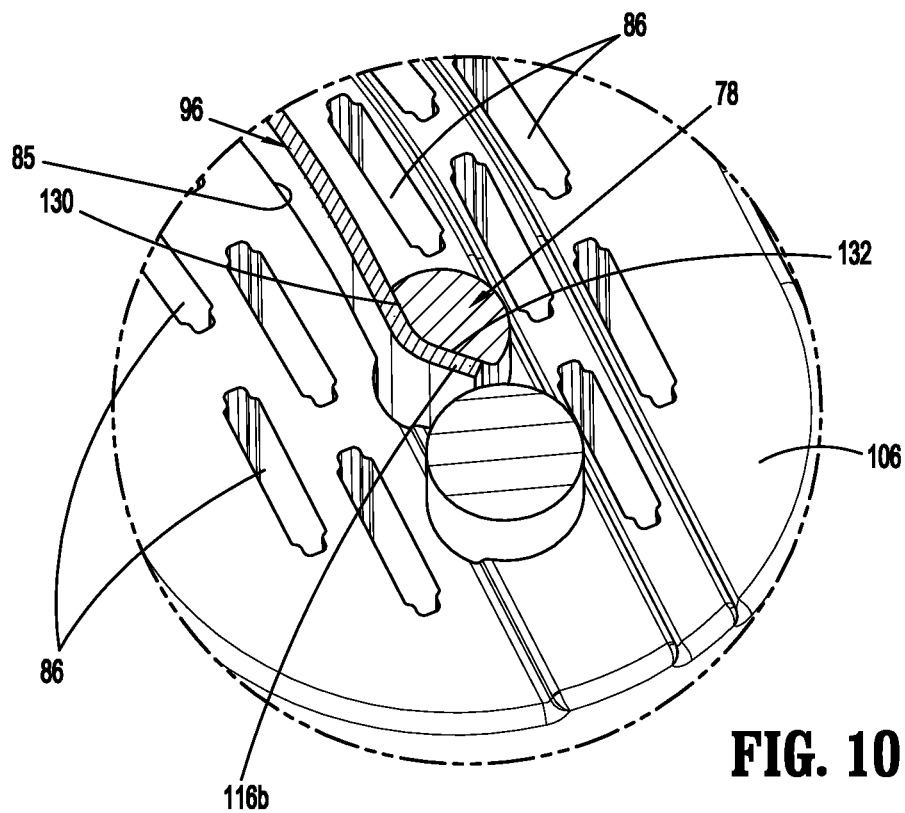
FIG. 10 is an enlarged view of the indicated area of detail shown in FIG. 9.
Figure 11:
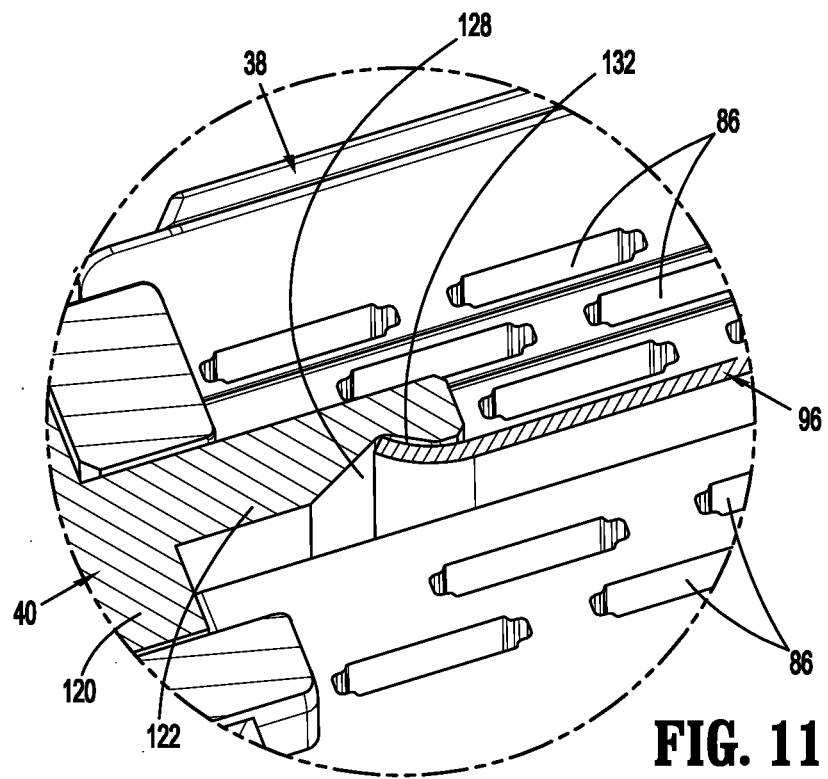
FIG. 11 is an enlarged view of the indicated area of detail shown in FIG. 9.
Figure 12:
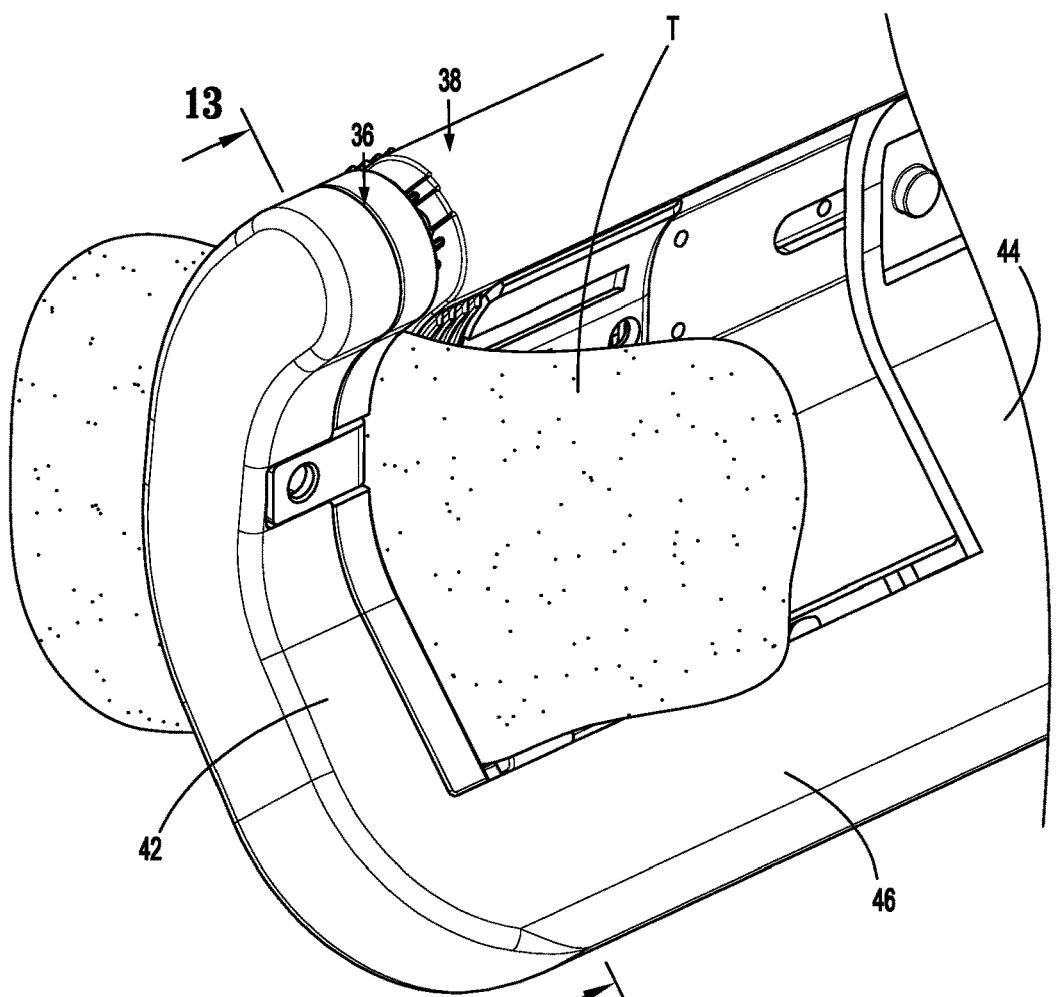
FIG. 12 is a side perspective view of the end effector of the surgical stapling device shown in FIG. 1 with the end effector in a clamped position about tissue.
Figure 13:
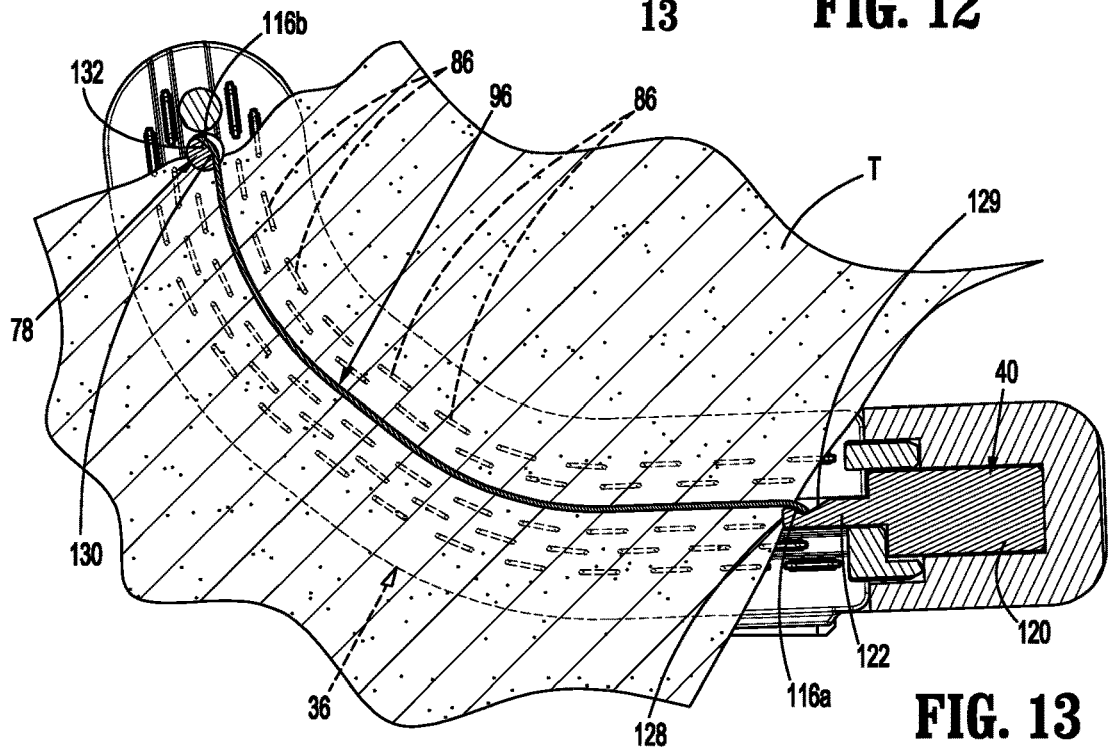
FIG. 13 is a cross-sectional view taken along section line 13-13 of FIG. 12.

FIGS. 4 and 4A illustrate the guide member 40 of the end effector 16. The guide member 40 includes a body portion 120 and a guide portion 122. The body portion 120 is fixedly secured within a longitudinal channel 126 (FIG. 9) defined in the longitudinal portion 46 of the body 34 of the end effector 16 such that the guide portion 122 extends transversely from the body portion 120 into the cavity 48 of the body 34 of the end effector 16. In aspects of the disclosure, the body portion 120 of the guide member 40 defines openings 127 (FIG. 4) that receive screws or rivets (not shown) to secure the guide member 40 to the body 34 of the end effector 16. The guide portion 122 of the guide member 40 extends longitudinally within the cavity 48 along substantially the length of the cavity 48 and defines a longitudinally extending angled guide surface 128 that receive the bent end portion 116*b* of the knife blade 96. In aspects of the disclosure, the angled guide surface 128 defines a portion of a longitudinally extending concavity 129 (FIG. 4). When a cartridge assembly 38 is received within the body 34 of the end effector 16, the guide portion 122 extends into the cartridge body 70 and engages the first bent end portion 116*a* of the knife blade 96 (FIG. 11). In aspects of the disclosure, the first bent end portion 116*a* of the knife blade 96 engages the angled guide surface 128 of the guide portion 122 of the guide member 40.

Figure 5:
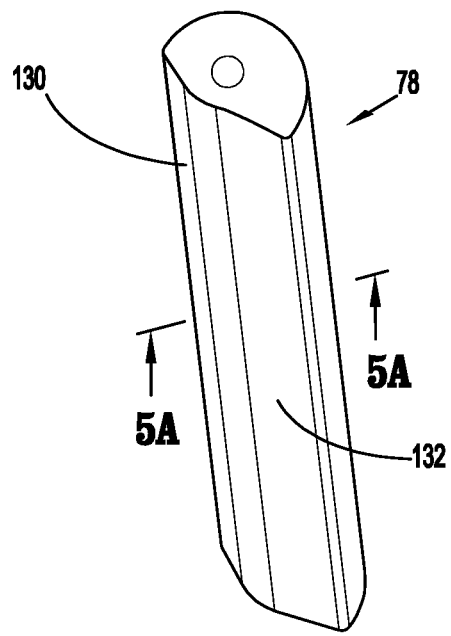
FIG. 5 is a side perspective view of a guide pin of the cartridge assembly shown in FIG. 2.
Figure 5A:
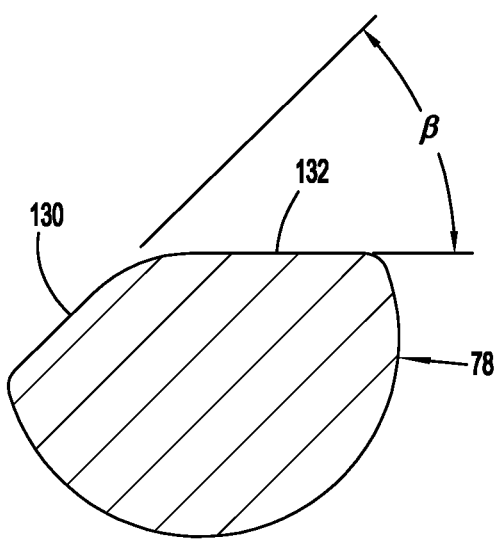
FIG. 5A is a cross-sectional view taken along section line 5A-5A of FIG. 2.
Figure 6:
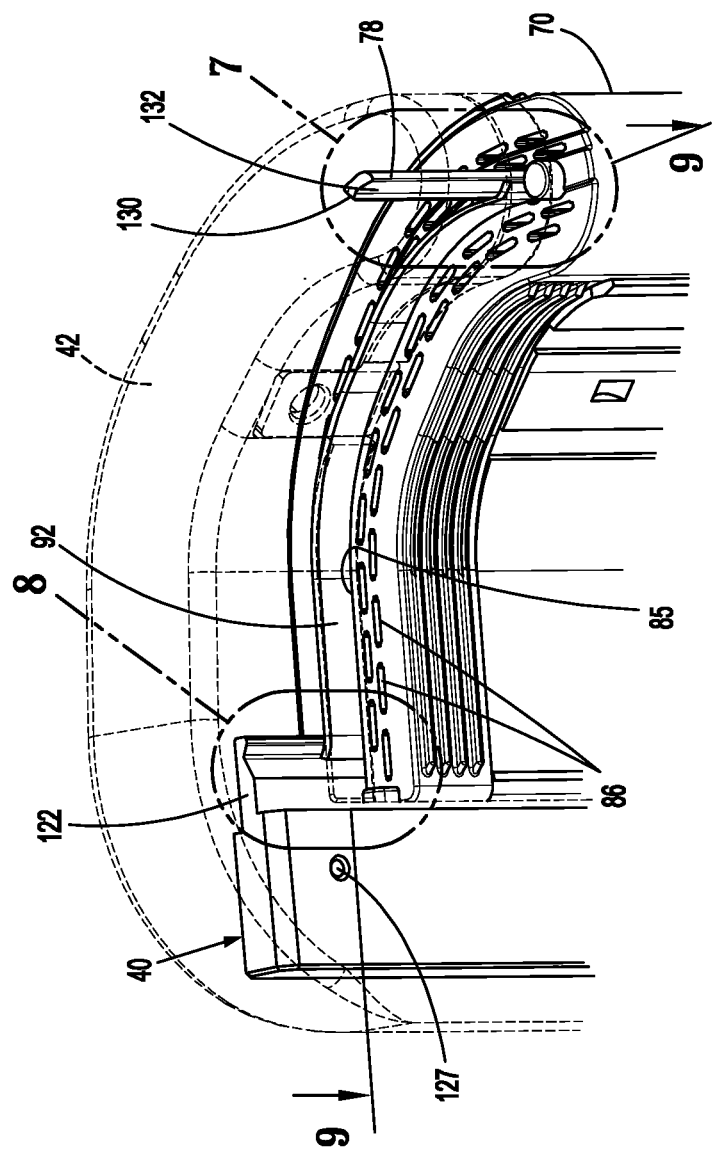
FIG. 6 is a side perspective view of a distal portion of the end effector of the stapling device shown in FIG. 1 with a portion of the end effector shown in phantom.
Figure 8:
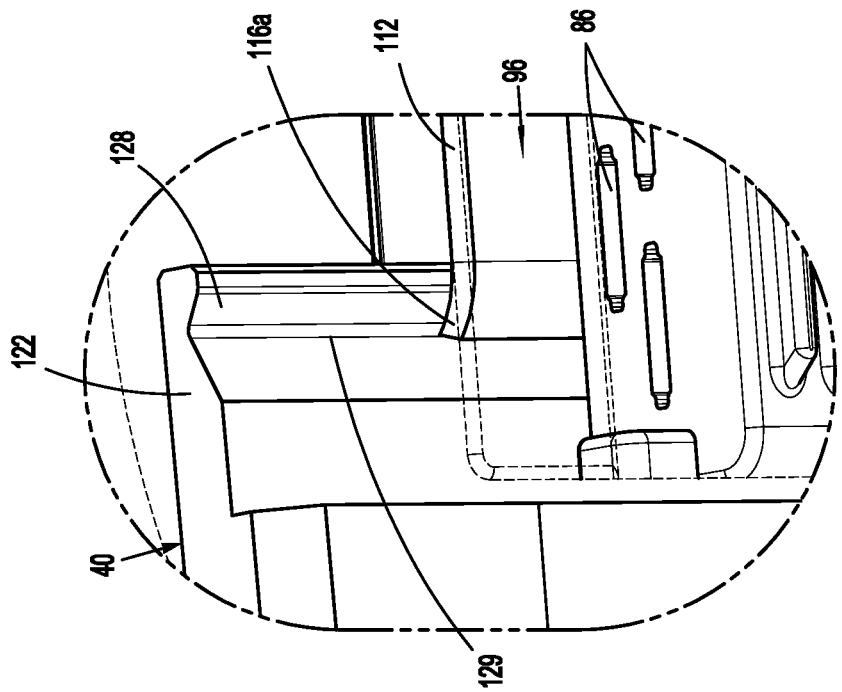
FIG. 8 is an enlarged view of the indicated area of detail shown in FIG. 6.
Figure 7:
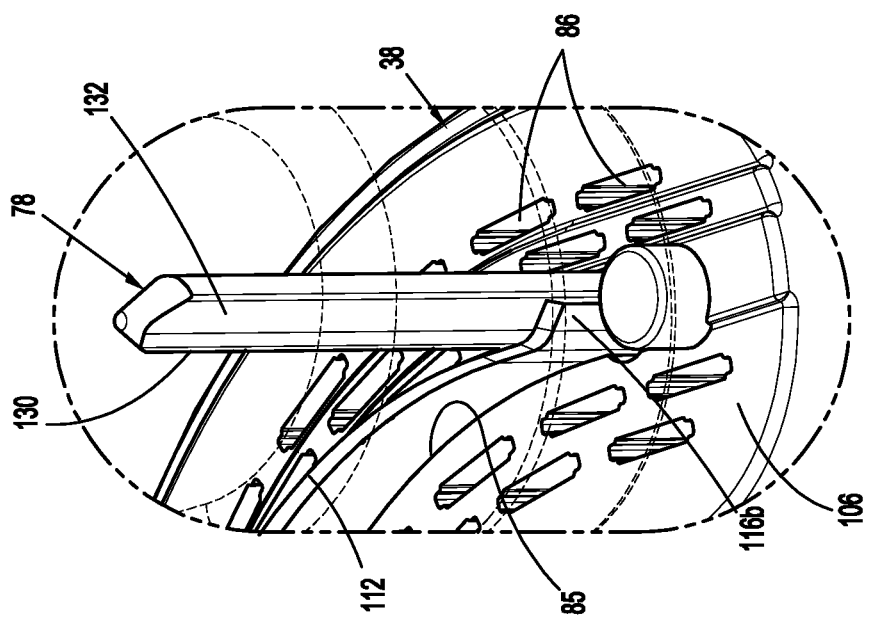
FIG. 7 is an enlarged view of the indicated area of detail shown in FIG. 6.

FIGS. 2, 5, and 5A illustrate the guide pin 78 of the cartridge assembly 38. The guide pin 78 has a semi-circular cross-sectional shape and includes a flat 130 and a guide surface 132 that have axes that define an acute angle β (FIG. 5A). The guide pin 78 is supported within the cartridge body 70 such that the wing 118 of the knife blade 96 is in sliding engagement with the flat 130 of the guide pin 78 and the second bent end portion 116*b* is in sliding engagement with the guide surface 132 of the guide pin 78.

FIGS. 6-13 illustrate the end effector 17 of the stapling device 10 with the stapling device 10 clamped about tissue and fired and the guide pin 78 in an advanced position. With the guide pin 78 in an advanced position, tissue "T" (FIG. 12) is confined within the cavity 48 in the body 34 of the end effector 16 between the anvil assembly 36 and the cartridge assembly 38. In the fired position, the knife blade 96 is in its advanced position with the cutting edge 112 (FIG. 8) of the knife blade 96 engaged with the anvil assembly 36. As the knife blade 96 moves from its retracted position towards its advanced position, the first bent end portion 116*a* of the knife blade 96 is engaged with and slides along the angled guide surface 128 of the guide portion 122 of the guide member 40 and the second bent end portion 116*b* of the knife blade 96 is engaged with and slides along the guide surface 132 of the guide pin 78. Engagement between the end portions 116*a* and 116*b* of the knife blade 96 with the guide surface 128 of the guide member 40 and the guide surface 132 of the guide pin 78 prevents outward spread of the clamped tissue "T" to maintain the tissue in the path of the cutting edge 112 of the knife blade 96 to effectively and cleanly cut the tissue "T" clamped between the anvil assembly 36 and the cartridge assembly 38. As described above, in aspects of the disclosure, the cutting edge 112 of the knife blade 96 extends across the first and second end bent end portions of the knife blade 96. This facilitates cutting of tissue "T" at the sides of the tissue "T" adjacent the ends of the knife blade 96.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stapling device comprising:
a handle portion;
an elongate body defining a longitudinal axis and extending distally from the handle portion; and
an end effector supported on the elongate body, the end effector including:
a body including a first portion, a second portion, and a longitudinal portion interconnecting the first and second portions, the first and second portions extending in a direction transverse to the longitudinal axis and having corresponding curved configurations, the first and second portions having first and second ends, the first portion spaced from the second portion to define a cavity therebetween that is closed at the first ends of the first and second portions by the longitudinal portion, the second ends of the first and second portions spaced from each other to define an opening;
a guide member secured to the longitudinal portion of the body of the end effector, the guide member including a guide portion that extends into the cavity, the guide portion defining an angled guide surface;
an anvil assembly supported on the first portion of the body of the end effector; and
a cartridge assembly including a cartridge body defining a body cavity, a pusher, a knife assembly, and a guide pin, the cartridge body defining staple receiving slots and a knife slot, the staple receiving slots positioned on opposite sides of the knife slot, each of the staple receiving slots including a staple, the pusher movable within the body cavity from a retracted position to an advanced position to eject the staples from the cartridge body, the knife assembly including a curved knife blade that is movable from a retracted position recessed within the cartridge body to an advanced position extending through the knife slot of the cartridge body, the guide pin including an angled guide surface and being movable from a retracted position located within the cartridge body to an advanced position extending from the cartridge body, the guide pin being engaged with the anvil assembly in its advanced position to close the opening defined by the body of the end effector, the knife blade having a curved configuration that corresponds to the curved configuration of the first and second portions of the body of the end effector and including first and second bent end portions, the first bent end portion engaged with the angled guide surface of the guide member and the second bent end portion engaged with the angled guide surface of the guide pin.

2. The stapling device of claim 1, wherein the knife blade has a concave side and a convex side and the first and second bent end portions are angled in a direction of the convex side of the knife blade away from the concave side.

3. The stapling device of claim 2, wherein the knife blade includes a distal portion that defines a cutting edge.

4. The stapling device of claim 3, wherein the cutting edge extends along the first and second bent end portions of the knife blade.

5. The stapling device of claim 1, wherein the guide member includes a body portion that is secured to the longitudinal portion of the body of the end effector, the guide portion extending from the body portion of the guide member into the cavity defined by the body of the end effector.

6. The stapling device of claim 5, wherein the guide portion defines a longitudinally extending concavity that is defined in part by the angled guide surface of the guide portion.

7. The stapling device of claim 1, wherein the knife assembly includes a knife holder, the knife blade secured to and extending distally from the knife holder.

8. The stapling device of claim 1, wherein the anvil assembly includes an anvil member and a cutting plate, the cutting plate being sandwiched between the first portion of the body of the end effector and the anvil member.

9. The stapling device of claim 1, wherein the second portion of the body of the end effector defines a first channel, the cartridge assembly being removably received within the first channel of the second portion of the body of the end effector.

10. The stapling device of claim 1, wherein the knife blade includes a central body portion and wings that extend outwardly from the central body portion, the first and second bent end portions of the knife blade extending outwardly from the wings.

11. The stapling device of claim 1, wherein the guide pin defines a flat and the flat and the angled guide surface of the guide pin define axes that intersect to define an acute angle.

12. The stapling device of claim 1, wherein the guide pin has a proximal portion, the proximal portion of the guide pin be connected to a pin coupler.

13. An end effector comprising:
a body including a first portion, a second portion, and a longitudinal portion interconnecting the first and second portions, the first and second portions extending in a direction transverse to the longitudinal portion and having corresponding curved configurations, the first and second portions having first and second ends, the first portion spaced from the second portion to define a cavity therebetween that is closed at the first ends of the first and second portions by the longitudinal portion, the second ends of the first and second portions spaced from each other to define an opening therebetween;
a guide member secured to the longitudinal portion of the body of the end effector, the guide member including a guide portion that extends into the cavity, the guide portion defining a first angled guide surface;
an anvil assembly supported on the first portion of the body of the end effector;
a cartridge assembly including a cartridge body defining a body cavity, a pusher, a knife assembly, and a guide pin, the cartridge body defining staple receiving slots and a knife slot, the staple receiving slots positioned on opposite sides of the knife slot, each of the staple receiving slots including a staple, the pusher movable within the body cavity from a retracted position to an advanced position to eject the staples from the cartridge body, the knife assembly including a curved knife blade that is movable from a retracted position recessed within the cartridge body to an advanced position extending through the knife slot of the cartridge body, the guide pin including a second angled guide surface and movable from a retracted position located within the cartridge body to an advanced position extending from the cartridge body, the guide pin engaged with the anvil assembly in its advanced position to close the opening defined by the body of the end effector, the knife blade having a curved configuration that corresponds to the curved configuration of the first and second portions of the body of the end effector and including first and second bent end portions, the first bent end portion engaged with the first angled guide surface of the guide member and the second bent end portion engaged with the second angled guide surface of the guide pin.

14. The end effector of claim 13, wherein the knife blade has a concave side and a convex side and the first and second bent end portions are angled in a direction of the convex side of the knife blade away from the concave side.

15. The end effector of claim 13, wherein the knife blade includes a distal portion that defines a cutting edge, the cutting edge extending along the first and second bent end portions.

16. The end effector of claim 13, wherein the guide member includes a body portion that is secured to the longitudinal portion of the body of the end effector, the guide portion extending from the body portion of the guide member into the cavity defined by the body of the end effector.

17. The end effector of claim 13, wherein the guide portion defines a longitudinally extending concavity that is defined in part by the angled guide surface of the guide portion.

18. The end effector of claim 13, wherein the anvil assembly includes an anvil member and a cutting plate, the cutting plate being sandwiched between the first portion of the body of the end effector and the anvil member.

19. The end effector of claim 13, wherein the knife blade includes a central body portion and wings that extend outwardly from the central body portion, the first and second bent end portions of the knife blade extending outwardly from the wings.

\* \* \* \* \*